(12) United States Patent
Ocvirk et al.

(10) Patent No.: US 9,879,298 B2
(45) Date of Patent: Jan. 30, 2018

(54) ENZYME STABILIZATION IN ELECTROCHEMICAL SENSORS

(71) Applicant: Roche Diabetes Care, Inc., Indianapolis, IN (US)

(72) Inventors: Gregor Ocvirk, Nierstein (DE); Claudia Gaessler-Dietsche, Schriesheim (DE)

(73) Assignee: ROCHE DIABETES CARE, INC., Indianapolis, IN (US)

(*) Notice: Subject to any disclaimer, the term of this patent is extended or adjusted under 35 U.S.C. 154(b) by 0 days.

(21) Appl. No.: 14/308,049

(22) Filed: Jun. 18, 2014

(65) Prior Publication Data

US 2015/0008141 A1    Jan. 8, 2015

Related U.S. Application Data

(63) Continuation of application No. 13/296,871, filed on Nov. 15, 2011, now abandoned, and a continuation of application No. PCT/EP2010/056668, filed on May 14, 2010.

(30) Foreign Application Priority Data

May 15, 2009    (EP) .................... 09160421

(51) Int. Cl.
  *G01N 27/327*    (2006.01)
  *G01N 33/50*    (2006.01)
  *C12Q 1/00*    (2006.01)
(52) U.S. Cl.
  CPC ............ *C12Q 1/006* (2013.01); *C12Q 1/001* (2013.01)

(58) Field of Classification Search
CPC ... C12Q 1/00; C12Q 1/54; C12Q 1/02; C12Q 1/006; C12Q 1/34; G01N 27/327; G01N 27/3272; G01N 27/48; G01N 27/26
See application file for complete search history.

(56) References Cited

U.S. PATENT DOCUMENTS

| 4,340,448 A * | 7/1982 | Schiller ................ C12Q 1/005 204/403.1 |
| 5,334,296 A * | 8/1994 | Henkens et al. ........... 205/777.5 |
| 7,563,588 B2 * | 7/2009 | Gao et al. ...................... 435/14 |
| 2005/0241957 A1 * | 11/2005 | Mao et al. .................. 205/777.5 |
| 2006/0021881 A1 | 2/2006 | Soundarrajan et al. |
| 2007/0029195 A1 | 2/2007 | Li et al. |
| 2008/0014471 A1 | 1/2008 | Kim |
| 2008/0044911 A1 | 2/2008 | Bock et al. |

(Continued)

FOREIGN PATENT DOCUMENTS

| EP | 0247850 A1 | 12/1987 |
| EP | 0603154 A2 | 6/1994 |

(Continued)

OTHER PUBLICATIONS

Yin et al.,Sensors and Actuators B, 76, 2001 187-192.*

(Continued)

*Primary Examiner* — Gurpreet Kaur
(74) *Attorney, Agent, or Firm* — Harness Dickey (57) ABSTRACT

The present invention relates to a composition for forming an electrode, an electrochemical sensor comprising the same, and a method for determining an analyte using the electrochemical sensor.

26 Claims, 9 Drawing Sheets

(56) References Cited

U.S. PATENT DOCUMENTS

2009/0071846 A1    3/2009   Staib et al.
2010/0187107 A1    7/2010   Katsuki et al.

FOREIGN PATENT DOCUMENTS

| JP | 06281614 | * | 7/1994 | ........... G01N 24/327 |
| WO | 2008007719 A1 | | 1/2008 | |

OTHER PUBLICATIONS

Zhu et al., Biosensors and Bioelectronic 23, 2007 528-535.*
Betancor et al., Preparation of a very stable immobilized biocatalyst of glucose oxidase from Aspergillus niger, Journal of Biotechnology 121:284-289 (2006).
Cho et al., Enzyme Immobilization on Activated Carbon: Alleviation of Enzyme Deactivation by Hydrogen Peroxide, Biotechnology and Bioengineering vol. XIX:769-775 (1977).
Guan et al., Glucose biosensor based on multi-wall carbon nanotubes and screen printed carbon electrodes, Biosensors and Bioelectronics 21:508-512 (2005).
Jeykumari et al., A novel nanobiocomposite based glucose biosensor using neutral red functionalized carbon nanotubes, Biosensors and Bioelectronics 23:1404-1411 (2008).
Karyakin et al., Improvement of Electrochemical Biosensors Using Enzyme Immobilization from Water-Organic Mixtures with a High Content of Organic Solvent, Analytical Chemistry 68(24):4335-4341(1996).
Kotel'Nikova et al., Non-aqueous enzymology approach for improvement of biosensors. Optimisation of Nafion-(glucose oxidase) membrane, Electronic Journal of Biotechnology, Poster abstract from the 2nd International Conference on Protein Stabilisation, 2000, http://www.ejbiotechnology.info/feedback/proceedingss/04/poster/p64.html.
Kurusu et al., Electrocatalytic Activity of Bamboo-Structured Carbon Nanotubes Paste Electrode Toward Hydrogen Peroxide, Analytical Letters 39:903-911 (2006).
Li et al., Biocomposites of covalently linked glucose oxidase on carbon nanotubes for glucose biosensor, Anal Bioanal Chem 383:918-922 (2005).
Lukachova et al., The improvement of polyaniline glucose biosensor stability using enzyme immobilization from water-organic mixtures with a high content of organic solvent, Sensors and Actuators B 44:356-360 (1997).
Rege et al., Enzyme-Polymer-Single Walled Carbon Nanotube Composites as Biocatalytic Films, Nano Letters 3 (6):829-832 (2003).
Tang et al., Amperometric glucose biosensor based on adsorption of glucose oxidase at platinum nanoparticle-modified carbon nanotube electrode, Analytical Biochemistry 331:89-97 (2004).
Tsai et al., Cast Thin Film Biosensor Design Based on a Nafion Backbone, a Multiwalled Carbon Nanotube Conduit, and a Glucose Oxidase Function, Langmuir 21:3653-3658 (2005).
Wang et al., Miniaturized Glucose Sensors Based on Electrochemical Codeposition of Rhodium and Glucose Oxidase onto Carbon-Fiber Electrodes, Analytical Chemistry 64(4):456-459 (1992).
Wang et al., Enzyme-dispersed carbon-nanotube electrodes: a needle microsensor for monitoring glucose, Analyst 128:1382-1385 (2003).
Wang et al., Carbon nanotube screen-printed electrochemical sensors, Analyst 129:1-2 (2004).
Wang et al., Carbon-nanotubes doped polypyrrole glucose biosensor, Analytica Chimica Acta 539:209-213 (2005).
Weetall, Covalent Coupling Methods for Inorganic Support Materials, Methods Enzymol. 44:134-148 (1976).
Office Action dated Nov. 18, 2016 in the corresponding Chinese Patent Application No. 201080019693.9.

* cited by examiner

ENZYME STABILIZATION IN ELECTROCHEMICAL SENSORS

CROSS-REFERENCE TO RELATED APPLICATIONS

This application is a continuation of U.S. patent application Ser. No. 13/296,871, filed Nov. 15, 2011, which is a continuation of International Application No. PCT/EP2010/056668, filed May 14, 2010, which claims the benefit and priority of European Patent Application No. 09160421.5, filed May 15, 2009. The entire disclosures of the above applications are incorporated herein by reference.

BACKGROUND

The present invention relates to a composition for forming an electrode, an electrochemical sensor comprising the same, and a method for determining an analyte using the electrochemical sensor.

Measuring systems for biochemical analysis are important components of clinically relevant analytical methods. This primarily concerns the measurement of analytes which can be directly or indirectly determined with the aid of enzymes. Determination of the concentration of clinically useful parameters is generally carried out using in vitro analytical systems. However, when determining analytes which show a significant change in their concentration during the course of the day an in vitro analysis is inappropriate due to limited temporal resolution and the difficulties encountered with sampling.

In this case, biosensors, i.e., measuring systems equipped with biological components, which allow a repeated measurement of the analyte either continuously or discontinuously and which can be used ex vivo as well as in vivo have proven to be particularly suitable for the measurement of analytes. Ex vivo biosensors are typically used in flow-through cells whereas in vivo biosensors can, for example, be implanted into subcutaneous fatty tissue. In this connection one distinguishes between transcutaneous implants which are only introduced into the tissue for a short period and are in direct contact with a measuring device located on the skin, and full implants which are inserted surgically into the tissue together with a measuring device.

Electrochemical biosensors which comprise an enzyme as a biological component contain the enzyme in or on the working electrode in which case for example the analyte can serve as a substrate for the enzyme and can be physicochemically altered (e.g. oxidized) with the aid of this enzyme. The electrical measuring signal generated by the flow of electrons released during conversion of the analyte on the working electrode correlates with the concentration of the measured analyte such that the electrical measuring signal can be used to determine the presence and/or the amount of the analyte in the sample.

In practice, a working electrode must fulfill a number of requirements in order to be suitable in electrochemical sensors:

The working electrode should have a low contact resistance and hence should be highly conductive.

The working electrode should not comprise any components which are electrochemically converted in the selected polarisation voltage. This can be accomplished by a suitable choice of binders and fillers.

The electrochemically active surface area of the working electrode has to be kept constant over its entire period of operation. For this purpose, a reduction of the surface area due to the adsorption of components of the surrounding fluid has to be avoided. This is generally affected by applying one or several polymer coatings, which are highly biocompatible.

The electrochemical reaction of the conversion product of the enzymatic reaction should be effected at a low overpotential in order to minimize the decomposition voltage and hence enable a specific conversion of the parameter. For this purpose, a fast transfer of electrons from the prosthetic group of the enzyme to the diverting electrode is to be provided.

The working electrode should comprise a sufficient amount of analyte-specific enzyme having sufficient and constant activity in order to guarantee that the enzymatic reaction superposed to the electrochemical conversion is not limited by the available enzymatic activity, but by the available amount of analyte. In other words, the sensitivity has to be maintained throughout the entire period of operation. A diffusion of the enzyme from the working electrode into the surrounding tissue has to be avoided, also for the reason of a possible toxicity of the enzyme. Finally, it has to be provided for that the enzymatic activity does not fall below a predetermined limit during storage.

A plurality of electrode compositions is known for minimizing overpotentials. As regards $H_2O_2$, the oxidation potential can be reduced, for example, by 450 mV by using rhodium- and glucose oxidase-coated carbon fibres as compared to carbon fibres coated with glucose oxidase alone (Wang et al., Analytical Chemistry (1992), 64, 456-459). A method which is simpler to realize is described in EP 0 603 154 A2, which document provides an electrode composite produced by thoroughly mixing oxides and/or hydroxides of elements of the 4th period of the periodic table with graphite and a binder, leading to a reduction in overvoltage of the anodic $H_2O_2$ oxidation by >200 mV.

In addition to electrically nonconductive and/or semiconductive metal oxides generally introduced into electrode composites, electrically conductive electrocatalysts such as carbon nanotubes are known, which, due to their small size, may be arranged in proximity to the prosthetic centre of the enzyme, have a high electric conductivity and enable an efficient transfer of electrons (Wang et al., Analyst (2003), 128, 1382-1385; Wang et al., Analyst (2004), 129, 1-2; Wang et al., Analytica Chimica Acta (2005), 539, 209-213; Shobha Jeykumari et al., Biosensors and Bioelectronics (2008), 23, 1404-1411). Due to their high surface area, small amounts of nanotubes are sufficient to obtain a reduction of the decomposition potential (US 2006/0021881 A1).

Different measures are known in the art in order to provide for a constant enzyme activity. One possibility to avoid enzyme diffusion from the surface of the working electrode into the environment is to provide the working electrode with a suitable coating, e.g. a cover membrane. However, the use of such coatings in electrochemical sensors is associated with certain problems such as the necessity to deposit pinhole-free membranes. Secondly, the cover membrane must be deposited with a highly reproducible layer thickness for mass transfer limited systems. This requirement represents an extensive restriction of possible coatings since the realization of very thin layers exhibiting a sufficiently high barrier to mass transfer is difficult to realize.

Moreover, electrochemical sensors which are used to determine different analytes must usually also contain different cover membranes in order to provide different mass transfer rates of the substrate and co-substrate to the electrode. At the same time it must be ensured that the cover membranes are highly biocompatible for in vivo applications. Since even the smallest defects in the membrane are sufficient to result in a bleeding of the enzyme from the electrode into the environment, an enormous amount of quality control is necessary especially in the case of in vivo biosensors, resulting in considerable technical requirements and increased production costs.

Alternatively, the extent of enzyme bleeding can be reduced by immobilizing the enzyme in the electrode matrix of the working electrode which has led to an intensive search for suitable immobilization methods for enzymes in electrochemical biosensors. In practice, the enzyme may either be coupled to one or more paste components in a chemically covalent manner or be inserted physically into a composite so that the enzyme is adsorptively bonded to one or several paste components and/or is incorporated therein.

As regards adsorptive immobilization, Rege et al. (Nano Letters (2003), 3, 829-832) disclose an electrode composite comprising single-wall carbon nanotubes (SWCNT) and/or graphite as conductive fillers and PMMA as binder, wherein chymotrypsin is physically retained. In this context, it was found out that SWCNT-containing composites show less enzyme bleeding than graphite-containing ones, which seems to be due to a higher surface energy of the SWCNTs as compared to graphite.

Tang et al. (Analytical Biochemistry (2004), 331, 89-97) showed that by using a CNT-electrode, onto which Pt particles were electrochemically deposited and which was adsorptively modified with glucose oxidase, the long-term stability of glucose oxidase can be significantly increased as compared to a conventional graphite electrode.

Tsai et al. (Langmuir (2005), 21, 3653-3658) disclose a stable glucose sensor which comprises a carbon electrode coated with a composite containing multi-wall carbon nanotubes (MWCNTs), Nafion and glucose oxidase. The immobilizing effect of the matrix is referred to the electrostatic interaction of negatively charged MWCNTs and Nafion on the one hand, and positively charged glucose oxidase on the other hand.

Guan et al. (Biosensors and Bioelectronics (2005), 21, 508-512) realize a glucose sensor by dispensing a MWCNT-containing suspension and a GOD- and a ferricyanide-containing solution onto a screenprinted carbon electrode. An increased linearity of the response curve was observed and attributed to an increased electron transfer rate of the MWCNTs as compared to that of a conventional carbon electrode.

Kurusu et al. (Analytical Letters (2006), 39, 903-911), finally, disclose that the use of an electrode comprising a mixture of MWCNT, GOD and mineral oil leads to a significant reduction of the oxidative decomposition voltage of $H_2O_2$.

However, adsorptive immobilization procedures suffer from a number of problems. A major disadvantage of physical immobilization is the dependency of the binding constant on the composition of the medium surrounding the electrode, requiring a barrier membrane to prevent enzyme leakage.

In particular, however, physical coupling makes heavy demands on the reproducibility of the effective surface of the working electrode and, thus, on the production thereof. As described above, adsorptive immobilization either requires an application of enzyme-containing solutions and/or suspensions onto the surface of a prefabricated working electrode or an introduction of enzyme-containing solutions and/or suspensions into an electrode composite. The dispensing application of enzyme-containing solutions and/or suspensions onto the surface of a working electrode, however, has the disadvantage that an addition of small volumes of enzyme solution, for example a volume in the range of nanoliters, makes high demands on the precision of an automated dosing apparatus. Furthermore, the distribution of enzyme on the surface of the working electrode and transfer of enzyme into the pores of the working electrode depends on the topography and the energy of the electrode's surface, which is difficult to reproduce.

In view of the above, the admixture of enzymes into an electrode composite is to be preferred. However, a loss of the effective enzyme activity caused by shearing, the influence of solvents and thermal impact cannot be avoided due to the requirement of a homogeneous distribution of enzymes in mostly hydrophobic composites. Moreover, restrictions with respect to overall paste conductivity and adhesion onto the substrate have to be taken into account since specific rheological characteristics are required for the deposition of the electrode paste, while a constant consistency of the paste after homogeneous distribution of a dry enzyme in the composite has to be provided.

As an alternative, the enzyme may be introduced into the composite in an aqueous solution or in a suspension in order to minimize denaturation. This, however, brings about the necessity of a subsequent removal of solvent or suspension agent so that the composite cannot be supposed to have constant rheological characteristics over the production period.

Hence, in view of the disadvantages of an adsorptive immobilization there is thus a concrete need to immobilize enzymes in electrochemical biosensors by covalent bonds to at least one component of the electrode matrix.

EP 0 247 850 A1 discloses biosensors for the amperometric detection of an analyte. These sensors contain electrodes with immobilized enzymes which are immobilized or adsorbed onto the surface of an electrically conducting support where the support consists of a platinized porous layer of resin-bound carbon or graphite particles or contains such a layer. For this purpose, electrodes made of platinized graphite and a polymeric binding agent are firstly prepared and these are subsequently brought into contact with the enzyme. In this case, the enzyme is immobilized either by adsorption to the electrode surface or by coupling it to the polymeric binding agent using suitable reagents.

Amperometric biosensors with electrodes comprising an enzyme immobilized or adsorbed onto or into an electrically conducting, porous electrode material are also described in EP 0 603 154 A2. In order to produce the enzyme electrodes, an oxide or oxide hydrate of a transition metal of the fourth period, such as for example manganese dioxide, acting as a catalyst is worked into a paste together with graphite and a non-conducting polymeric binding agent, and the porous electrode material obtained after drying the paste is brought into contact with the enzyme in a second step. The enzyme can be immobilized on or in the porous electrode material by using a cross-linking reagent such as glutardialdehyde.

A major disadvantage of the electrochemical biosensors described in EP 0 247 850 A1 and EP 0 603 154 A2 is that the enzyme is first immobilized on the electrode that has been prefabricated without enzyme. As a consequence, there is the problem that the enzyme cannot be coupled to the electrode components in a controlled manner. Thus, when glutardialdehyde is used as a cross-linking reagent, the enzyme not only binds in an uncontrolled manner to any reactive components of the electrode material, but it is also inter-crosslinked. Furthermore, this procedure contaminates the electrode with the reagents that are used and, hence, the electrode has to again be thoroughly cleaned especially before use in an in vivo biosensor which increases the production complexity and thus the costs.

Cho et al. (Biotechnology and Bioengineering (1977), 19, 769-775) describe the immobilization of enzymes on activated carbons by covalent coupling. More particularly, the immobilization of glucose oxidase to petroleum-based activated carbons by (a) adsorption of the enzyme followed by cross-linking with glutaraldehyde or (b) activation of the carbon surface with a diimide and subsequent reaction with the enzyme is described. By this means, a considerably slower deactivation of the enzyme in the presence of $H_2O_2$ could be shown as compared to the soluble enzyme.

Li et al. (Analytical and Bioanalytical Chemistry (2005), 383, 918-922) disclose a glucose biosensor comprising a modified glassy carbon electrode as the working electrode. The modified glassy carbon electrode is prepared by coating a commercial electrode's surface with a dispersion of functionalized multi-wall carbon nanotubes (MWCNTs) having oxidized glucose oxidase covalently attached thereto in PBS buffer solution which contains Nafion® and ferrocene monocarboxylic acid. The catalytic effect of the functionalized nanotubes for glucose oxidation is particularly emphasized.

US 2007/0029195 A1 discloses immobilization of biomolecules such as proteins by covalent coupling to a conductive polymeric matrix reinforced by nanoparticles to improve the mechanical stability, electrical conductivity and immobilization of biomolecules. The matrix is a nanocomposite comprising gold nanoparticles coated with a polypyrrole formed from pyrrole and pyrrole propylic acid, wherein the latter compound provides for the covalent attachment of the biomolecules.

US 2008/0014471 A1 discloses electrochemical sensors comprising electrodes employing cross-linked enzyme clusters immobilized on carbon nanotubes (CNTs). In detail, the immobilization involves functionalization of the nanotubes' surface, subsequent covalent attachment of an enzyme such as glucose oxidase by means of a linking reagent to yield a CNT-enzyme conjugate, precipitation of free enzymes with a precipitation agent, and final treatment with a cross-linking reagent to form cross-linked enzyme clusters covalently attached to the CNTs via the CNT-enzyme conjugate.

US 2008/044911 A1 discloses a glucose sensor comprising nanowires having glucose oxidase covalently attached to their surface, which functionalized nanowires are prepared by contacting conventional nanowires with a linking reagent, e.g. a silane, and the enzyme. Conversion of glucose in a sample to be examined by the glucose oxidase immobilized on the nanowires' surface results in a change in pH of the test solution, wherein this change in pH produces a signal in the nanowires which can be detected by suitable means.

It is known in the art that covalent coupling of an enzyme to a support (e.g. MANAE-agarose, activated glyoxyl agarose and glutaraldehyde agarose) leads to a stabilization of the enzyme against thermal decomposition (Betancor et al., Journal of Biotechnology (2006), 121, 284-289). However, in addition to thermal decomposition, biosensors employing such immobilized enzymes also face the problem of enzyme decomposition caused by organic solvents during storage of the biosensor or caused by oxidative agents such as $H_2O_2$ during the period of operation.

In practice, biosensors must fulfill a plurality of requirements in order to allow exact measurements for immediate or time-delayed therapeutic measures. In particular, it is of uppermost importance that the analyte of interest can be determined with both a high specificity and sensitivity in order to enable determination of low amounts of the clinically relevant parameter. Consequently, the significant loss in enzymatic activity generally observed in commercially available biosensors when storing the same for more than one month is not acceptable for diagnostical and/or clinical purposes.

SUMMARY

Hence, an object of the invention is to provide a composition for forming an electrode, in which the disadvantages of the prior art are at least partially eliminated. In particular, the composition should ensure a specific and durable immobilization of the enzyme, prevent or at least reduce the loss of enzymatic activity upon production of the electrode composites, storage for a period of more than one month as well as biosensor function, and guarantee a high sensitivity over the whole period of operation.

The invention provides compositions for forming an electrode, the compositions comprising an electrically conductive component having an analyte-specific enzyme covalently attached thereto, wherein the composition further comprises at least one electrically nonconductive or semi-conductive enzyme-stabilizing component.

According to the invention, the composition comprises an electrically conductive component having an analyte-specific enzyme covalently attached thereto. The term "electrically conductive component" as used within the present application refers to any material containing free-moveable electric charges and having a resistivity of $p<10^{-4}$ $\Omega$cm, thereby allowing the transport of electric current. The electrically conductive material may be an electronic conductor (first order conductor) or an ion conductor (second order conductor), with an electronic conductor being preferred.

Preferably, the electrically conductive component is a $H_2O_2$-decomposition catalyst. This means that the electrically conductive component does not only transport electric current, but is additionally able to catalyze the decomposition of hydrogen peroxide which is present or formed in a sample contacting the electrically conductive component. Since hydrogen peroxide generally causes damage to most of the enzymes used in the detection of clinically relevant analytes and additionally can act as an inhibitor of the analyte or of co-substrates such as oxygen, the decomposition of hydrogen peroxide in biochemical test elements is of crucial importance. For this purpose, the electrically conductive component may, for example, catalyze the chemical conversion of hydrogen peroxide to a chemically less active or inert substance, including the oxidation of hydrogen peroxide to water.

In another preferred embodiment of the present invention, the electrically conductive component is selected from the group consisting of activated carbon, carbon black, graphite, carbonaceous nanotubes, palladium, platinum, and hydroxides of iron oxide such as for example FeO(OH), with graphite and carbonaceous nanotubes being especially preferred.

The term "carbonaceous nanotubes" as used herein refers to all kinds of nanotubes; i.e., tubes having an average inner diameter of <1 comprising carbon as one of their components. In particular, carbonaceous nanotubes in the sense of the present invention comprise carbon nanotubes (CNT) which may be in the form of, for example, single-wall carbon nanotubes (SWCNT), double-wall carbon nanotubes (DWCNT), multi-wall carbon nanotubes (MWCNT), etc. Since nanotubes generally provide a high effective surface, they can be extensively modified with suitable substances to be immobilized on their surface, such as for example enzymes employed in the detection of an analyte.

In another embodiment, the composition according to the invention may comprise at least one additional electrically conductive component in addition to the electrically conductive component having the analyte-specific enzyme covalently attached thereto. The additional electrically conductive component may be any material capable of transporting electric current and is preferably selected from the group consisting of activated carbon, carbon black, graphite, carbonaceous nanotubes, palladium, platinum, and hydroxides of iron oxide. This component may, in principle, also form a conjugate with the analyte-specific enzyme by means of covalent bonds, but preferably is not covalently attached to the analyte-specific enzyme.

According to the invention, the electrically conductive component has an analyte-specific enzyme covalently attached thereto. The enzyme may be any enzyme which is specific for the analyte to be detected and which appears to be suitable to a person skilled in the art for achieving the desired effect. The enzyme immobilized on the electrically conductive component is preferably an oxidase and in particular alcohol oxidase (1.1.3.13), arylalcohol oxidase (EC 1.1.3.7), catechol oxidase (EC 1.1.3.14), cholesterol oxidase (EC 1.1.3.6), choline oxidase (1.1.3.17), galactose oxidase (EC 1.1.3.9), glucose oxidase (EC 1.1.3.4), glycerol-3-phosphate oxidase (EC 1.1.3.21), hexose oxidase (EC 1.1.3.5), malate oxidase (EC 1.1.3.3), pyranose oxidase (EC 1.1.3.10), pyridoxine-4-oxidase (EC 1.1.3.12) or thiamine oxidase (EC 1.1.3.23). More preferably, the enzyme is glucose oxidase.

Preferably, the analyte-specific enzyme is selectively covalently bound to the electrically conductive component. The covalent binding of the enzyme to the electrically conductive component ensures the constancy of the function of an electrode comprising the inventive composition because a detachment of enzyme can be ruled out under the typical measurement conditions (physiological electrolyte concentration, physiological pH, body temperature). Thus, electrochemical sensors comprising such electrodes remain operational over a long time period and virtually operate free of drift.

In order to covalently bind the analyte-specific enzyme to the electrically conductive component, the present invention envisages in a preferred embodiment that the electrically conductive component has a surface comprising functional groups to which the enzyme is bound. The surface can, for example, exhibit hydroxy, carboxy or amino functionalities. Alternatively, the surface can be functionalized by coating the electrically conductive component with a suitable reagent to form functional groups by means of which the enzyme can be covalently bound to the surface of the electrically conductive component.

Coating reagents which are used within the scope of the present invention are substances which, on the one hand, undergo a covalent binding with the electrically conductive component and, on the other hand, contain at least one functional group which serves to covalently bind the enzyme. This means that the coating reagents are at least bifunctional; i.e., comprise at least two functional groups which may be the same or different.

In a preferred embodiment, the enzyme is directly covalently bound to the surface of the electrically conductive component, which means that at least one covalent bond is formed between a functional group of the enzyme and a functional group on the surface of the electrically conductive component. The enzyme can be coupled to the surface in any manner and can comprise a prior activation of functional groups on the surface of the electrically conductive component and/or of the enzyme.

Functional groups can for example be activated by reacting the functionalized electrically conductive component and/or the enzyme with a suitable activation reagent. Preferred activation reagents comprise carbodiimides such as for example dicyclohexylcarbodiimide (DCC), diisopropylcarbodiimide or 1-ethyl-3-(3-dimethylaminopropyl)carbodiimide (EDC) as well as combinations of carbodiimides and succinimides. A particularly suitable activation reagent for the purposes of the present invention comprises a combination of 1-ethyl-3-(3-dimethylaminopropyl)-carbodiimide (EDC) and N-hydroxysuccinimide (NHS).

Other methods suitable for covalently binding, in particular selectively covalently binding the analyte-specific enzyme to the electrically conductive component are known to a person skilled in the art and are described, for example, in H. Weetall, Methods of Enzymology (1976), 33, 134-148.

According to the invention, the composition further comprises an electrically nonconductive or semiconductive enzyme-stabilizing component. The term "electrically nonconductive component" as used within the present application refers to any material having a resistivity of $\rho > 10^9$ $\Omega$cm and incapable of transporting electric current. In contrast, the term "electrically semiconductive component" as used herein refers to any material having a resistivity of $10^{-4}$ ? $\rho$ ? $10^9$ $\Omega$cm. The term "enzyme-stabilizing" means that the nonconductive or semiconductive component is able to stabilize the analyte-specific enzyme by either reacting with the analyte-specific enzyme to form a complex or conjugate with the enzyme or by converting chemical substances causing decomposition of the enzyme.

In a preferred embodiment, the electrically nonconductive or semiconductive enzyme-stabilizing component is a $H_2O_2$-decomposition catalyst which means that the electrically nonconductive or semiconductive enzyme-stabilizing component decomposes hydrogen peroxide, for example by chemical conversion, in order to prevent a damage to the analyte-specific enzyme employed in the composition according to the present invention.

The electrically nonconductive or semiconductive enzyme-stabilizing component is preferably selected from the group consisting of an $H_2O_2$-degrading metal oxide and an $H_2O_2$-degrading enzyme. For the purpose of the present invention the $H_2O_2$-degrading metal oxide may be any metal oxide which is able to catalyze the decomposition of hydrogen peroxide for example by oxidizing the same, with $Ag_2O$, $Al_2O_3$ or an oxide of a metal of the 4th period of the periodic table having proven to be particularly advantageous. The oxide of a metal of the 4th period of the periodic table is preferably an oxide of Mn, CuO or ZnO, wherein $MnO_2$, $Mn_3O_4$ or $Mn_5O_8$ are especially preferred. The $H_2O_2$-degrading enzyme may be any enzyme known to decompose hydrogen peroxide and particular encompasses a peroxidase and catalase.

In another preferred embodiment, the composition according to the invention further comprises the analyte-specific enzyme covalently attached to the electrically nonconductive or semiconductive enzyme-stabilizing component. This means that the analyte-specific enzyme employed in the inventive composition may not only be covalently attached to the electrically conductive component but can additionally be covalently attached to the electrically nonconductive or semiconductive enzyme-stabilizing component by means of covalent bonds formed between the enzyme and, for example, functional groups on the surface of the electrically nonconductive or semiconductive enzyme-stabilizing component.

The electrically conductive component and/or the electrically nonconductive or semiconductive enzyme-stabilizing component may be provided according to the invention in a particulate form, wherein the particle size can be varied depending on the respective requirements. In a preferred embodiment, the composition according to the invention comprises the electrically conductive component and/or the electrically nonconductive or semiconductive enzyme-stabilizing component in the form of nanoparticles; i.e., particles having an average diameter of <1 μm. Within the scope of the present invention 90% of the nanoparticles usually have a diameter of 10 nm to 100 nm, a diameter of 15 nm to 30 nm having proven to be particularly preferred.

The ability to control the effective surface of the electrically conductive component and/or the electrically nonconductive or semiconductive enzyme-stabilizing component by means of the particle size is of crucial importance, for example, with respect to a functionalization with chemical substances. More particularly, a higher effective surface can increase the loading with enzyme and, thus, can result in a higher enzyme activity stated in units per milligram of enzyme-loaded component. The electrically conductive component used for the purposes of the present invention usually has an enzyme activity of about 10 mU/mg to about 5 U/mg, with an enzyme activity of about 100 mU/mg to about 1 U/mg having proven to be particularly advantageous. The term "unit" as used within the scope of the present application represents the amount of enzyme which is required to convert 1 μmol substrate per minute under standard conditions.

In addition to the electrically conductive component and the electrically nonconductive or semiconductive enzyme-stabilizing component the composition according to the invention may comprise other components conventionally employed for forming an electrode such as, for example, binders, fillers and the like. As regards binders, the composition preferably comprises at least one binder selected from the group consisting of fluorinated hydrocarbons such as Teflon®, polycarbonates, polyisoprene, polyurethanes, acrylic resins, polyvinyl resins and silicones, with polyurethanes, acrylic resins and polyvinyl resins being more preferred.

For forming an electrode, the electrically conductive component having the analyte-specific enzyme covalently attached thereto, the electrically nonconductive or semiconductive enzyme-stabilizing component and all other components required to form an electrode matrix are thoroughly mixed and subsequently dried such that the electrically conductive component and/or the electrically nonconductive or semiconductive enzyme-stabilizing component are preferably homogeneously dispersed in the composition.

Depending on the specific requirements of the electrode to be formed, the skilled person is able to determine the amounts of the different components required for providing a composition according to the invention without any difficulty. As regards the electrically conductive component, however, it has been proven as advantageous when the composition contains the conjugate formed from the electrically conductive component and the analyte-specific enzyme in an amount of from 0.5 to 10% by weight, based on the dry weight of the composition. On the other hand, the composition preferably contains the electrically nonconductive or semiconductive enzyme-stabilizing component in an amount of from 5 to 50% by weight, based on the dry weight of the composition.

The composition described herein significantly reduces the loss of activity of analyte-specific enzyme required for detecting an analyte of interest by means of a biosensor such as, for example, an electrochemical sensor encompassing an electrode making use of the composition according to the invention. In particular, in the composition according to the invention the enzyme has a residual activity of at least 90% after storing the composition for at least 4 weeks, preferably at least 12 weeks, more preferably at least 28 weeks at a temperature of 4° C., based on the total activity of the enzyme before storage; i.e., based on the total activity of the enzyme in the composition directly after its preparation.

In another aspect, the present invention thus relates to an electrochemical sensor for determining an analyte, the sensor comprising at least one working electrode and at least one reference electrode, wherein the working electrode comprises the composition according to the invention.

Whereas the working electrode of the electrochemical sensor according to the invention serves to convert the analyte to be determined, the reference electrode allows to adjust the polarization potential of the working electrode and can consist of any material which is suitable for the purposes of the invention. A metal/metal ion electrode, in particular a silver/silver chloride electrode, is preferably used as the reference electrode. In addition to the at least one working electrode and the at least one reference electrode, the electrochemical sensor may also comprise at least one counter electrode which is preferably in the form of a noble metal electrode, in particular a gold electrode, or a graphite electrode.

According to the invention, the electrochemical sensor preferably comprises a biocompatible coating covering the at least one working electrode, the at least one reference electrode and optionally the counter electrode(s). The biocompatible coating allows the analyte to penetrate into the electrode matrix but should prevent electrode components from escaping into the surrounding medium containing the analyte of interest.

In view of the fact that due to the covalent binding of the enzyme to the electrically conductive component the enzyme does not bleed out of the working electrode or the electrochemical sensor, a biocompatible coating is not absolutely necessary for many applications. Thus, the electrochemical sensor according to the invention can also be used in in vivo applications when the biocompatible coating is not a barrier to enzymes. In such case, a biocompatible coating can be selected which provides an optimal interaction with the surrounding tissue and/or blood or serum.

Biocompatible coatings can be generated in various ways. A preferred method is to use prefabricated membranes which are applied to the electrochemical sensor. The membrane can be immobilized on the sensor by various techniques, with gluing or laser welding being regarded as preferred. Alternatively, the biocompatible coating can be generated in situ by applying a solution of a suitable polymer onto the electrochemical sensor and subsequently drying it. The application of the polymer onto the biosensor is preferably carried out by spraying, dip-coating or dispersing a dilute solution of the polymer in a low-boiling organic solvent, but is not limited to these methods.

Polymers which are suitable for such purposes comprise in particular polymers having a zwitterionic structure and mimicking cell surfaces such as for example 2-methacryloyloxyethyl-phosphorylcholine-co-n-butyl-methacrylate (MPC-co-BMA). The biocompatible coatings that are obtained usually have a thickness of about 1 µm to about 100 µm, preferably of about 3 µm to about 25 µm.

The electrochemical sensor according to the invention is preferably designed for multiple measurements; i.e., the sensor enables a repeated measurement of the analyte to be determined. This is particularly desirable in applications in which a constant, i.e., continuous or discontinuous control of the presence and/or the amount of an analyte is to take place over a longer time period of, e.g., one day or longer, in particular one week or longer. In a particularly preferred embodiment, the electrochemical sensor according to the invention thus is fully or partially implantable and can be implanted, for example, into fatty tissue or into blood vessels. Alternatively, the invention allows the electrochemical sensor to be designed as a flow-through cell through which a fluid sample containing the analyte is passed.

The electrochemical sensor described herein can be used to determine an analyte in a fluid medium which can originate from any source. In a preferred embodiment, the electrochemical sensor is used to determine an analyte in a body fluid comprising but not limited to whole blood, plasma, serum, lymph fluid, bile fluid, cerebrospinal fluid, extracellular tissue fluid, urine as well as glandular secretions such as saliva or sweat, wherein whole blood, plasma, serum and extracellular tissue fluid are regarded as particularly preferred. The amount of sample required to carry out the analysis is usually from about 0.01 µl to about 100 µl, preferably from about 0.1 µl to about 2 µl.

The analyte to be determined qualitatively and/or quantitatively can be any biological or chemical substance which can be detected by means of a redox reaction. The analyte is preferably selected from the group consisting of malic acid, alcohol, ammonium, ascorbic acid, cholesterol, cysteine, glucose, glutathione, glycerol, urea, 3-hydroxybutyrate, lactic acid, 5'-nucleotidase, peptides, pyruvate, salicylate and triglycerides. In a particularly preferred embodiment, the analyte to be determined by means of the electrochemical sensor according to the invention is glucose.

In yet a further aspect, the present invention relates to a method for determining an analyte, comprising the steps:
(a) contacting a sample containing the analyte with an electrochemical sensor according to the invention, and
(b) determining the presence and/or the amount of the analyte.

In order to determine the analyte, the electrochemical sensor can be designed in any manner which allows a contact between the electrochemical sensor and the sample containing the analyte. Thus, the sensor can be designed as a flow-through cell through which the medium containing the analyte flows. On the other hand, the sensor can also be designed as a diffusion sensor, wherein the contact between the sensor and medium takes place by diffusion. Equally, the electrochemical sensor can be designed as a device which is intended to be completely or partially implanted into the body of a patient, in which case it is implanted either into a blood vessel or into tissue and in particular into subcutaneous fatty tissue.

A measurable signal is generated by the sensor depending on the presence and/or the amount of analyte. This signal is preferably an electrical signal such as for example electrical current, voltage, resistance etc. which is evaluated or read-out using suitable means. The electrochemical sensor is preferably an amperometric sensor.

DRAWINGS

It is intended to further elucidate the invention by the following figures and examples.

FIG. 4 shows a decomposition rate of $H_2O_2$ [mM/mg/h] caused by different electrically conductive and electrically nonconductive or semiconductive materials:

FIG. 5 shows a measuring signal [nA] of different electrochemical sensors plotted against increasing glucose concentrations [mg/dl]. Polarisation voltage 350 mV:

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

EXAMPLES

Example 1—Preparation of a Conjugate Formed from Carbon Nanotubes and Glucose Oxidase (CNT-GOD)

For preparing an electrically conductive component having an enzyme covalently attached thereto, 2.5 g of carbon nanotubes (CNT, Nanolab) were added to a solution of 480 mg glucose oxidase (GOD, Roche), 9.6 g of 1-ethyl-3-(3- dimethylaminopropyl)-carbodiimide (EDC, Sigma), and 7.2 g of N-hydroxysuccinimide (NHS, Sigma) in 480 ml of Millipore water. After incubating the mixture for 6 hours at room temperature on a laboratory shaker, the mixture was passed through a membrane filter, thereby separating the conjugate from the reaction solution. The conjugate was washed with PBS buffer (3×120 ml), Millipore water (1×120 ml), and dried overnight under vacuum, yielding 3.0 g of CNT-GOD conjugate.

Example 2—Determination of the Enzymatic Activity of the CNT-GOD Conjugate

In order to determine the enzymatic activity of the CNT-GOD conjugate prepared in Example 1, 5 mg of lyophilized conjugate were suspended in 1 ml of MES buffer and stirred for 1 hour at room temperature. In parallel, Toyobo solution (GLO-201; 30 ml of MES buffer (79 mM); 6 ml of glucose solution (131 mM); 0.3 ml of 4-aminoantipyrine solution (0.2 mM); 0.3 ml of N-ethyl-N-(2-hydroxy-3-sulfopropyl)-m-toluidine solution (0.3 mM); 0.3 ml of peroxidase solution (about 4 U/ml)) was pipetted into a cuvette and tempered for 10 minutes at 37° C. After adding the conjugate to the tempered Toyobo solution, absorption of the mixture thus obtained was measured using a wavelength of 555 nm. By this means, the enzymatic activity was determined to be 870 mU/mg conjugate.

Example 3—Stability of an Electrochemical Sensor Employing a Working Electrode Comprising a CNT-GOD Conjugate and a $H_2O_2$-Decomposition Catalyst In order to determine the stability of an electrochemical sensor according to the present invention, a working electrode comprising an electrode matrix consisting of 78.25% by weight of an electrode paste (Acheson), 1.75% by weight of the CNT-GOD conjugate of Example 1 and 20% by weight of $MnO_2$ (Merck) was prepared.

Figure 1:
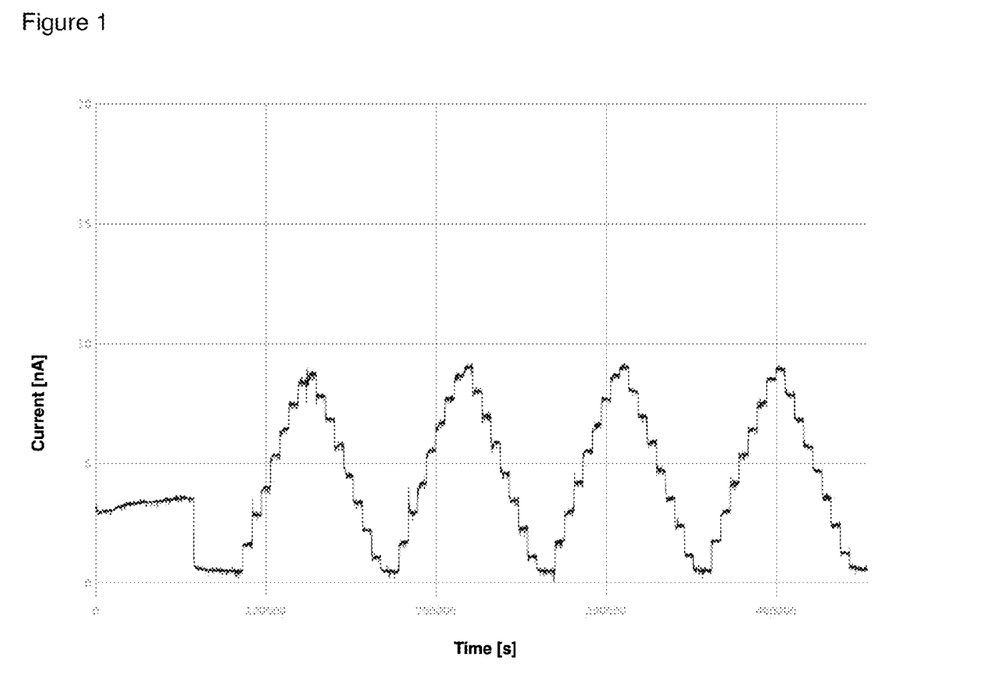
FIG. 1 shows a measuring signal [nA] of an electrochemical sensor according to the present invention plotted against time [s] in dependence on the glucose concentration [0, 2, 4, 6, 8, 12, 17, 23, 26, 20, 15, 10, 7, 5, 3, 0.8 mM], the sensor employing a working electrode comprising a conjugate formed from carbon nanotubes and glucose oxidase (CNT-GOD; 1.75% by weight) and $MnO_2$ (20% by weight) as semiconductive $H_2O_2$-decomposition catalyst. Polarisation voltage 350 mV.

Subsequently, the electrochemical sensor was contacted with a solution containing glucose at concentrations of 0, 2, 4, 6, 8, 12, 17, 23, 26, 20, 15, 10, 7, 5, 3 and 0.8 mM periodically varying over a period of 5 days. As can be derived from FIG. 1, the electrochemical sensor did not show any loss of sensitivity over the whole period which is a result of both prevention of enzyme bleeding caused by covalent binding to the carbon nanotubes and the decomposition of $H_2O_2$ catalyzed by $MnO_2$.

Example 4—Long-Term Stability of an Electrochemical Sensor Employing a Working Electrode Comprising a CNT-GOD Conjugate and a $H_2O_2$-Decomposition Catalyst In order to determine the long-term stability of an electrochemical sensor according to the present invention, a working electrode comprising an electrode matrix consisting of 78% by weight of an electrode paste (Acheson), 2.4% by weight of the CNT-GOD conjugate of Example 1 and 19.5% by weight of $MnO_2$ (Merck) was prepared.

Subsequently, the electrochemical sensor was stored over a period of 28 weeks at a temperature of 4° C. As becomes evident from FIG. 2, the measuring signal of the electrochemical sensor remains unchanged between week 4 and week 28 following its preparation. The loss of sensitivity between week 0 and week 4 is ascribed to conditioning effects of the electrode matrix.

Example 5—Determination of the Enzymatic Activity of a Composition Comprising a CNT-GOD Conjugate and a $H_2O_2$-Decomposition Catalyst In order to determine the enzymatic activity of a composition according to the present invention, 10 mg of a lyophilized CNT-GOD-conjugate were suspended in 1 ml of MES buffer (pH 7.4) and incubated for 1 hour at room temperature.

Figure 2:
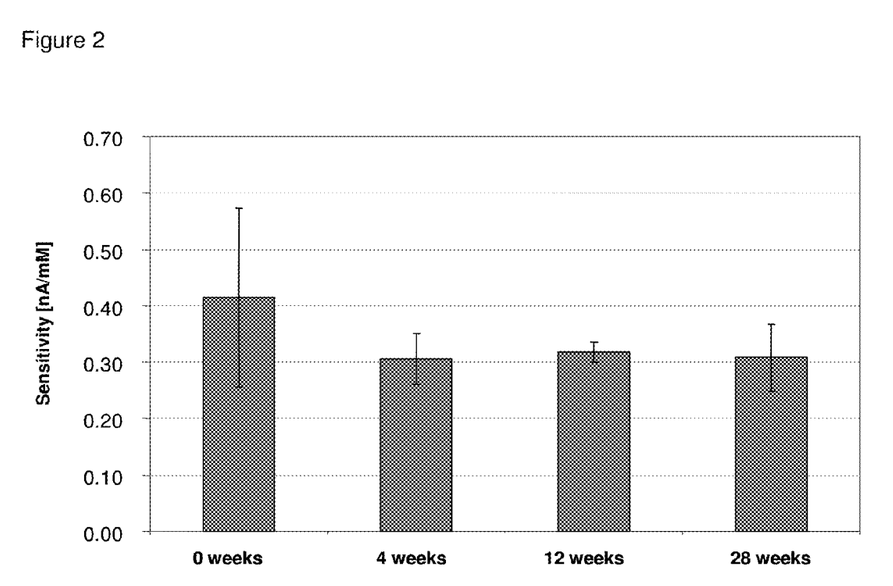
FIG. 2 shows a measuring signal [nA/mM] of an electrochemical sensor according to the present invention stored over a period of 28 weeks at a temperature of 4° C., the sensor employing a working electrode comprising a conjugate formed from carbon nanotubes and glucose oxidase (CNT-GOD; 2.4% by weight) and $MnO_2$ (19.5% by weight) as semiconductive $H_2O_2$-decomposition catalyst.

Subsequently, a commercially available $H_2O_2$ assay (Toyobo) was used to measure the residual enzymatic activity of the CNT-GOD conjugate, which was determined to be about 600 mU/mg lyophilized conjugate (cf. FIG. 2). In parallel, both the residual enzymatic activity of the CNT-GOD conjugate in MES buffer in the presence of $H_2O_2$ (5% solution) and the residual enzymatic activity of CNT-GOD in MES buffer in the presence of $H_2O_2$ (5% solution) and 500 U/ml of catalase were determined.

Figure 3:
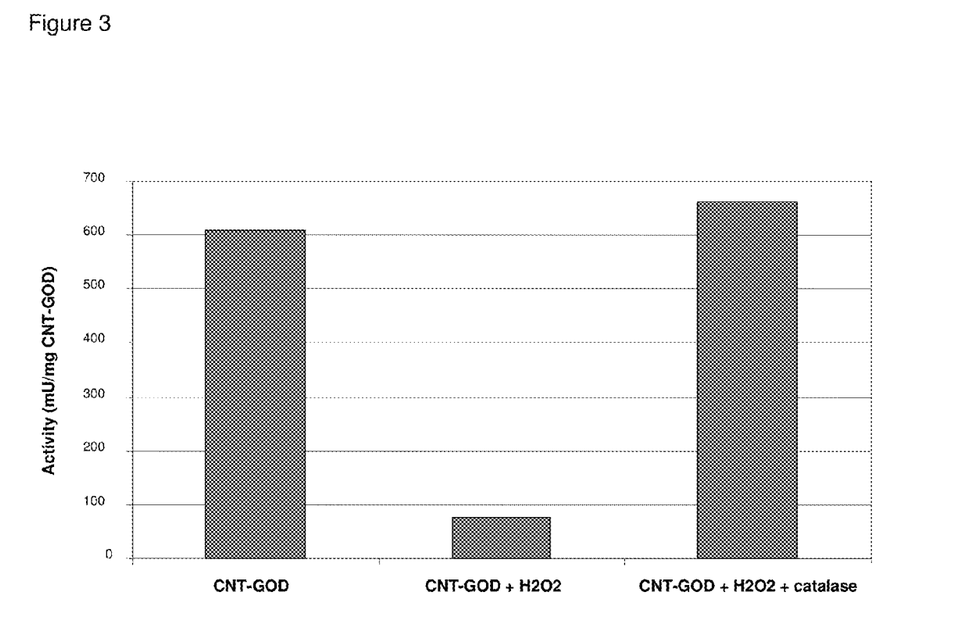
FIG. 3 shows enzymatic activity [mU/mg lyophilized conjugate] of a conjugate formed from carbon nanotubes and glucose oxidase (CNT-GOD) in MES buffer (pH 7.4), in MES buffer in the presence of $H_2O_2$ (5% solution), and in MES buffer in the presence of $H_2O_2$ (5% solution) and 500 U/ml of catalase.

As can be seen from FIG. 3, the residual enzymatic activity of the CNT-GOD conjugate decreased to less than 100 mU/mg lyophilized conjugate when $H_2O_2$ was present in the sample (CNT-GOD+$H_2O_2$). On the other hand, the addition of both $H_2O_2$ solution and the $H_2O_2$-decomposition catalyst catalase resulted in a residual enzymatic activity of about 650 mU/mg lyophilized conjugate (CNT-GOD+$H_2O_2$+ catalase), indicating complete repression of denaturation of GOD by $H_2O_2$.

Example 6—Determination of $H_2O_2$-Decomposition Catalysts

In order to determine compounds acting as $H_2O_2$-decomposition catalysts, a number of carbons and metal oxides have been evaluated with respect to their ability to effectively catalyze the decomposition of $H_2O_2$.

Figure 4A:
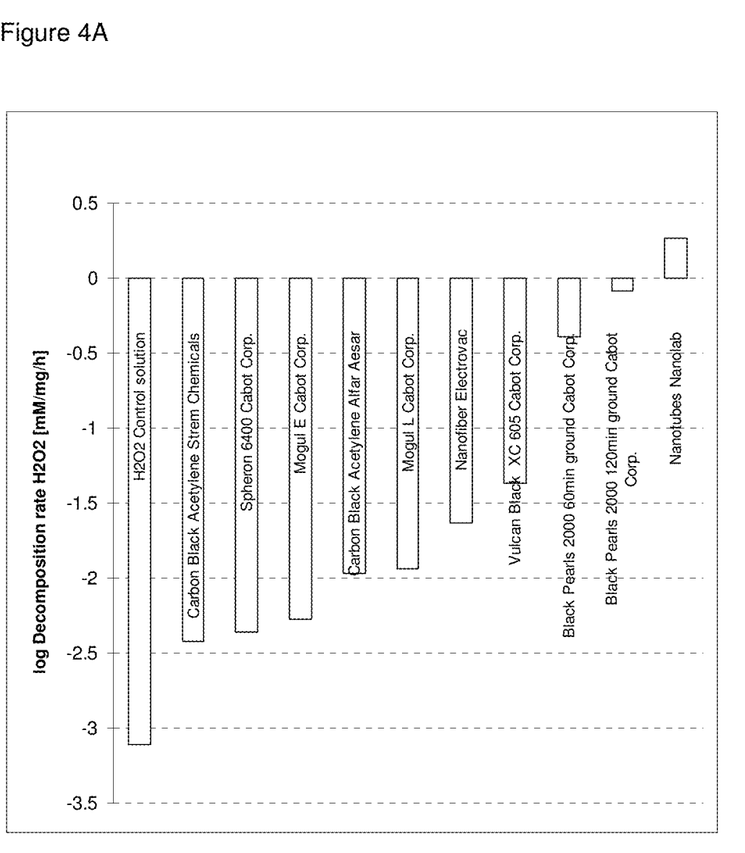
FIG. 4A shows a decomposition rate of $H_2O_2$ [mM/mg/h] caused by different commercially available carbons.

In detail, Carbon Black Acetylene (Strem Chemicals), Spheron 6400 (Cabot Corporation), Mogul E (Cabot Corporation), Carbon Black Acetylene (Alfa Aesar), Mogul L (Cabot Corporation), Nanofibers (Electrovac), Vulcan Black XC-605 (Cabot Corporation), Black Pearls 2000 (Cabot Corporation; ground for 60 min), Black Pearls 2000 (Cabot Corporation; ground for 120 min) and Nanotubes (Nanolab) were tested as electrically conductive carbon materials. In this context, carbon nanotubes (Nanolab) and Black Pearls 2000 (Cabot Corporation; ground for 120 min) were shown to be particularly suitable, providing a $H_2O_2$-decomposition rate of 0.00126 and 0.00098 mM/mg catalyst/h, respectively (cf. FIG. 4A).

Figure 4B:
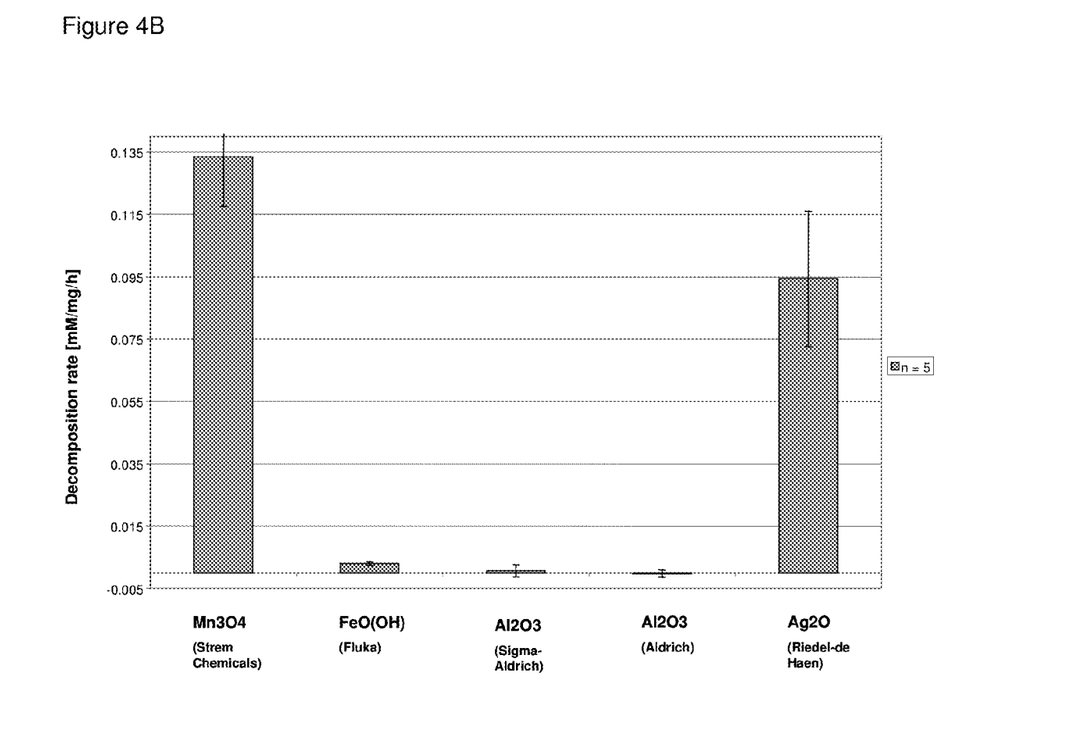
FIG. 4B shows a decomposition rate of $H_2O_2$ [mM/mg/h] caused by different commercially available metal oxides.
Figure 4C:
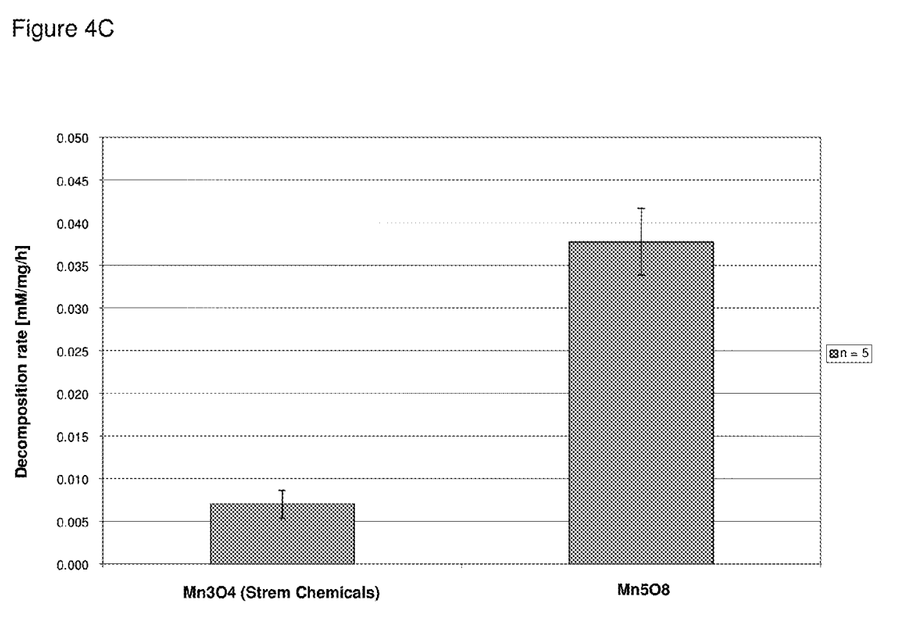
FIG. 4C shows a decomposition rate of $H_2O_2$ [mM/mg/h] caused by two different manganese oxides.

As regards the metal oxides, it becomes clear from FIGS. 4B and 4C that the different compounds employed in the test provide quite different decomposition rates. Whereas the catalytic effect of commercially available $Al_2O_3$ (Sigma-Aldrich, Product No. 229423), $Al_2O_3$ (Aldrich, Product No. 551643) and FeO(OH) (Fluka, Product No. 71063) was rather poor, $Ag_2O$ (Riedel-de Haën, Product No. 10228), and $Mn_3O_4$ (Strem Chemicals, Product No. 93-2513) were shown to be very effective as $H_2O_2$-decomposition catalysts (cf. FIG. 4B).

Another compound very effectively catalyzing the decomposition of $H_2O_2$ is $Mn_5O_8$ which was obtained by heating commercially available $Mn_3O_4$ (Strem Chemicals, Product No. 93-2513) in 6 hours from 25° C. to 430° C., holding this temperature for 12 hours, and subsequently cooling to 25° C. As can be derived from FIG. 4C, the decomposition rate of $H_2O_2$ observed in the presence of $Mn_5O_8$ obtained by the above procedure was significantly better than the catalyzing effect of $Mn_3O_4$.

Example 7—Reduction of Overpotential in an Electrochemical Sensor Employing a Working Electrode Comprising a CNT-GOD Conjugate and a $H_2O_2$-Decomposition Catalyst In order to determine the effect of an electrically nonconductive or semiconductive enzyme-stabilizing component on the overvoltage observed at the working electrode of electrochemical sensors, eight electrochemical sensors employing a working electrode comprising 2% by weight of the CNT-GOD conjugate of Example 1 and eight electrochemical sensors employing a working electrode comprising both 2% by weight of the CNT-GOD conjugate of Example 1 and 20% by weight of $MnO_2$ (Merck) were prepared.

Figure 5A:
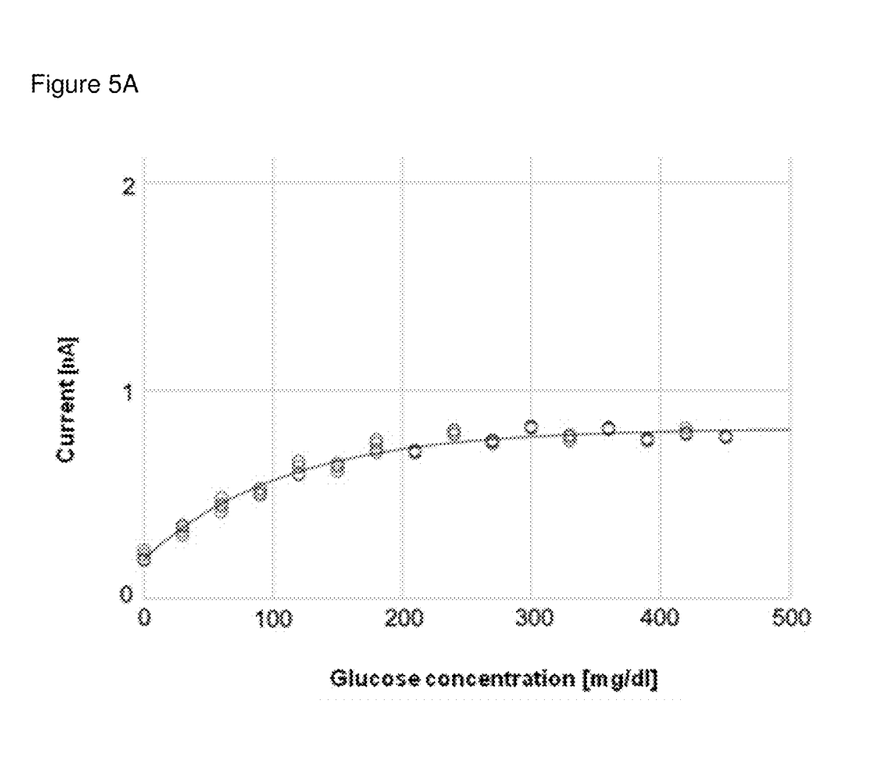
FIG. 5A shows a measuring signal [nA] of 8 electrochemical sensors employing a working electrode comprising a conjugate formed from carbon nanotubes and glucose oxidase (CNT-GOD; 2% by weight).

As becomes evident from FIG. 5A, the use of working electrodes comprising the CNT-GOD conjugate alone resulted in a low sensitivity of 0.01±0.03 nA/mM glucose solution when applying a polarisation voltage of 350 mV (relative to an Ag/AgCl reference electrode) and measuring the electric current in dependence on the glucose concentration.

Figure 5B:
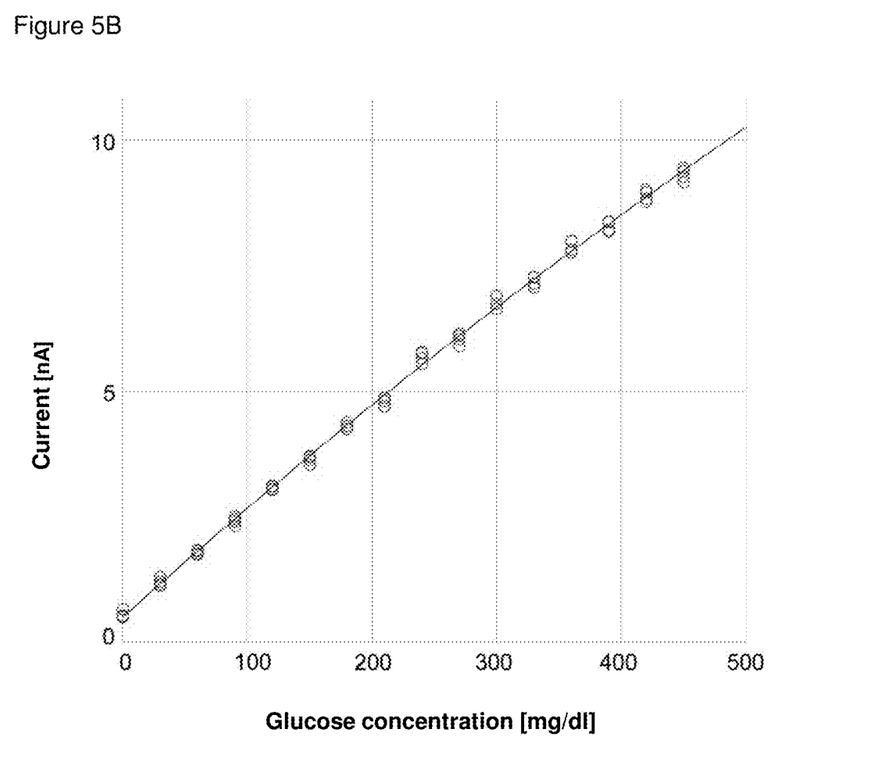
FIG. 5B shows a measuring signal [nA] of 8 electrochemical sensors according to the present invention, the sensors employing a working electrode comprising a conjugate formed from carbon nanotubes and glucose oxidase (CNT-GOD; 2% by weight) and $MnO_2$ (20% by weight) as semiconductive $H_2O_2$-decomposition catalyst.
Figure 6:
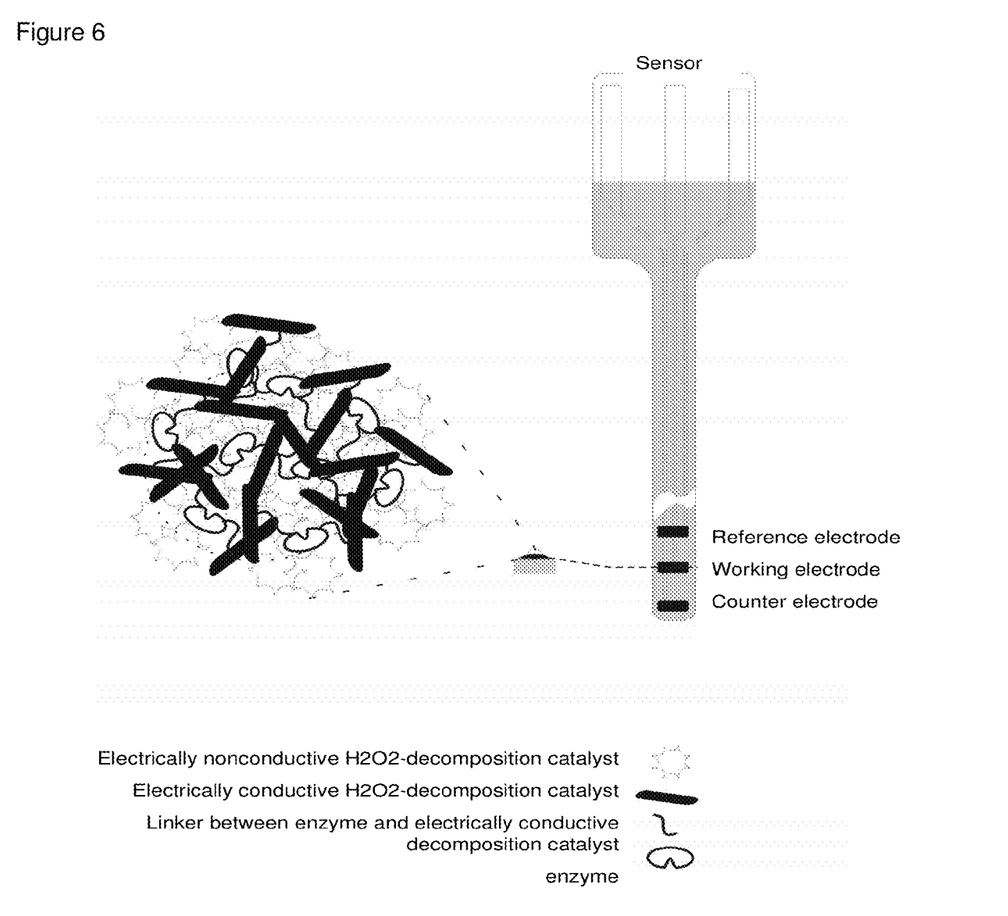
FIG. 6 shows a schematic representation of an electrochemical sensor according to the present invention.

In contrast, the use of working electrodes comprising the CNT-GOD conjugate in combination with $MnO_2$ resulted in a remarkably increased sensitivity of 0.54±0.11 nA/mM glucose solution under the same reaction conditions, indicating a significant reduction of overvoltage at the working electrode (cf. FIG. 5B).

What is claimed is:

1. A composition for forming an electrode, the composition comprising an electrically conductive component having an analyte-specific enzyme covalently bound only to the electrically conductive component, wherein the composition further comprises at least one electrically nonconductive or semiconductive component stabilizing the analyte-specific enzyme by converting chemical substances causing decomposition of the enzyme, and wherein the electrically conductive component and/or the electrically nonconductive or semiconductive component is provided in the form of nanoparticles.

2. The composition according to claim 1, wherein the electrically conductive component is a $H_2O_2$-decomposition catalyst.

3. The composition according to claim 1, wherein the electrically conductive component is selected from the group consisting of activated carbon, carbon black, graphite, carbonaceous nanotubes, palladium, platinum, and hydroxides of iron oxide.

4. The composition according to claim 3, wherein the electrically conductive component is selected from the group consisting of graphite and carbonaceous nanotubes.

5. The composition according to claim 1, wherein the enzyme is an oxidase.

6. The composition according to claim 5, wherein the enzyme is a glucose oxidase.

7. The composition according to claim 1, wherein the electrically nonconductive or semiconductive component is a $H_2O_2$-decomposition catalyst.

8. The composition according to claim 1, wherein the electrically nonconductive or semiconductive component is selected from the group consisting of an $H_2O_2$-degrading metal oxide and an $H_2O_2$-degrading enzyme.

9. The composition according to claim 8, wherein the electrically nonconductive or semiconductive component is $Ag_2O$, $Al_2O_3$ or an oxide of a metal of the 4th period of the periodic table.

10. The composition according to claim 8, wherein the $H_2O_2$-degrading enzyme is peroxidase or catalase.

11. The composition according to claim 9, wherein the oxide of a metal of the 4th period of the periodic table is $MnO_2$, $Mn_3O_4$ or $Mn_5O_8$, CuO or ZnO.

12. The composition according to claim 1, further comprising at least one binder selected from the group consisting of fluorinated hydrocarbons, polycarbonates, polyisoprene, polyurethanes, acrylic resins, polyvinyl resins and silicones.

13. The composition according to claim 1, wherein the electrically conductive component and/or the electrically nonconductive or semiconductive component is homogeneously dispersed in the composition.

14. The composition according to claim 1, wherein the enzyme has a residual activity of at least 90% after storing the composition for at least 4 weeks at a temperature of 4° C., based on the total activity of the enzyme before storage.

15. The composition according to claim 14, wherein the enzyme has a residual activity of at least 90% after storing the composition for at least 28 weeks at a temperature of 4° C., based on the total activity of the enzyme before storage.

16. An electrochemical sensor for determining an analyte, the sensor comprising at least one working electrode and at least one reference electrode, wherein the working electrode comprises the composition according to claim 1.

17. The electrochemical sensor according to claim 16, wherein it comprises a biocompatible coating covering the working electrode and the reference electrode.

18. The electrochemical sensor according to claim 16 for determining an analyte in a body fluid.

19. The electrochemical sensor according to claim 16 for determining an analyte selected from the group consisting of malic acid, alcohol, ammonium, ascorbic acid, cholesterol, cysteine, glucose, glutathione, glycerol, urea, 3-hydroxybutyrate, lactic acid, 5'-nucleotidase, peptides, pyruvate, salicylate and triglycerides.

20. The electrochemical sensor according to claim 19 for determining glucose.

21. A method for determining an analyte, comprising the steps:
(a) contacting a sample containing the analyte with an electrochemical sensor according to claim 16, and
(b) determining the presence and/or the amount of the analyte.

22. A composition for forming an electrode, the composition comprising an electrically conductive component having an analyte-specific enzyme covalently bound only to the electrically conductive component, wherein the composition further comprises at least one electrically nonconductive or semiconductive component stabilizing the analyte-specific enzyme by converting chemical substances causing decomposition of the enzyme, and at least one binder selected from the group consisting of fluorinated hydrocarbons, polycarbonates, polyisoprene, polyurethanes, acrylic resins, polyvinyl resins and silicones, and wherein the electrically conductive component and/or the electrically nonconductive or semiconductive component is homogeneously dispersed in the composition.

23. A composition for forming an electrode, the composition comprising:
an electrically conductive component having an analyte-specific enzyme covalently bound only to the electrically conductive component; and at least one electrically nonconductive or semiconductive component stabilizing the analyte-specific enzyme by converting chemical substances causing decomposition of the enzyme, wherein the at least one electrically nonconductive or semiconductive component is an $H_2O_2$-degrading metal oxide comprising $Ag_2O$, $Al_2O_3$ or an oxide of a metal of the 4th period of the periodic table.

24. The composition according to claim 23, wherein the $H_2O_2$-degrading metal oxide is selected from the group consisting of $MnO_2$, $Mn_3O_4$, $Mn_5O_8$, CuO, and ZnO.

25. The composition according to claim 23, wherein the electrically conductive component is a $H_2O_2$-decomposition catalyst.

26. The composition according to claim 23, wherein the electrically conductive component is selected from the group consisting of activated carbon, carbon black, graphite, carbonaceous nanotubes, palladium, platinum, and hydroxides of iron oxide.

* * * * *